US008992456B1

(12) United States Patent
Powell

(10) Patent No.: US 8,992,456 B1
(45) Date of Patent: Mar. 31, 2015

(54) IMPLANTABLE PUMP FOR REMOVAL OF CEREBROSPINAL FLUID

(76) Inventor: N. Garrett Powell, Nashville, TN (US)

(*) Notice: Subject to any disclaimer, the term of this patent is extended or adjusted under 35 U.S.C. 154(b) by 0 days.

(21) Appl. No.: 12/707,279

(22) Filed: Feb. 17, 2010

Related U.S. Application Data

(60) Provisional application No. 61/207,701, filed on Feb. 17, 2009.

(51) Int. Cl.
*A61M 1/00* (2006.01)
*A61B 5/00* (2006.01)
*A61M 5/142* (2006.01)
*A61M 5/168* (2006.01)

(52) U.S. Cl.
USPC ............... 604/8; 222/191; 222/190; 222/192; 222/630; 600/104

(58) Field of Classification Search
CPC ....... A61M 1/00; A61M 5/168; A61M 5/142; A61M 27/006; A61M 2202/0464; A61B 5/00; A61B 2010/0077
USPC .................. 604/8, 9; 222/191, 190, 192, 630; 600/104
See application file for complete search history.

(56) References Cited

U.S. PATENT DOCUMENTS

| 4,391,600 | A * | 7/1983 | Archibald ...................... 604/153 |
| 4,598,579 | A * | 7/1986 | Cummings et al. ............... 73/37 |
| 2004/0030279 | A1* | 2/2004 | Rubenstein et al. .............. 604/9 |
| 2005/0020962 | A1* | 1/2005 | Reich et al. ........................ 604/8 |
| 2006/0020239 | A1* | 1/2006 | Geiger et al. ..................... 604/9 |
| 2006/0111659 | A1* | 5/2006 | Tyler .................................. 604/9 |
| 2006/0149161 | A1* | 7/2006 | Wilson et al. ................. 600/561 |
| 2010/0130884 | A1* | 5/2010 | Linninger ..................... 600/547 |
| 2010/0305551 | A1* | 12/2010 | Lobl et al. .................. 604/891.1 |
| 2011/0224595 | A1* | 9/2011 | Pedersen et al. .................. 604/8 |
| 2012/0046596 | A1* | 2/2012 | Ludin et al. ....................... 604/9 |

* cited by examiner

*Primary Examiner* — Tatyana Zalukaeva
*Assistant Examiner* — Sara Sass
(74) *Attorney, Agent, or Firm* — Waller Lansden Dortch & Davis, LLP; Matthew C. Cox; Blake M. Bernard

(57) ABSTRACT

A device and system for removing cerebrospinal fluid (CSF) from a CSF space within a patient's body includes a housing adapted for implantation into a subcutaneous body space remote from the CSF space. A fluid pump is mounted inside the device housing. The pump has a pump actuator, a fluid inlet extending through the housing wall and a fluid outlet extending through the housing wall. A battery-powered electric motor is mounted inside the housing and is operatively coupled to the pump actuator. Device control circuitry controls operation of the electric motor. The device control circuitry includes a processor responsive to CSF space pressure signals, outflow pressure signals, and CSF flow rate signals to calculate CSF space pressures, CSF outflow pressures, and CSF removal volumes. A telemetry unit includes a transmitter to wirelessly transmit pump data and a receiver to receive external operational commands.

14 Claims, 3 Drawing Sheets

IMPLANTABLE PUMP FOR REMOVAL OF CEREBROSPINAL FLUID

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of the following patent application which is hereby incorporated by reference: U.S. Provisional Application No. 61/207,701, filed Feb. 17, 2009.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to implantable medical devices. More particularly, this invention pertains to medical devices used to remove cerebrospinal fluid (CSF) from a patient's CSF spaces for treatment of medical conditions.

Physicians treat certain illnesses and medical conditions, such as hydrocephalus, by removing excess CSF from CSF spaces in the afflicted patient's body. These CSF spaces can include the cerebral ventricles and subarachnoid space.

Conventionally, therapeutic removal of CSF can be accomplished using devices which are capable of collecting CSF from a CSF space, such as the intracranial ventricles, and moving the collected fluid to a location outside of the CSF space. In some cases, the removal location will be an internal body space such as the venous system or peritoneal cavity. Other conventional CSF removal techniques involve externally disposing of the CSF through a transcutaneous apparatus or shunt having a component for extracting the CSF from the CSF space, a component for disposing of the extracted CSF, and component for controlling the flow of the CSF through the apparatus. Some prior art methods and devices for removing CSF are disclosed in U.S. Pat. No. 6,575,928.

One of the weaknesses of prior art CSF shunts and methods is that they lack the ability to closely monitor and/or precisely regulate the flow of CSF through the device on a programmed or real time basis. Many treating physicians would find it helpful to have an easy and non-invasive way of monitoring the functioning of an implantable CSF removal device so that the operation of the device can be optimally adjusted to suit the needs of a particular patient. Such devices are lacking in the prior art.

BRIEF SUMMARY OF THE INVENTION

In one aspect, the present invention is device for removing cerebrospinal fluid (CSF) from a CSF space within a patient's body. The device has a housing with an outside wall. The housing is adapted for implantation of the device into a subcutaneous body space remote from the CSF space. A fluid pump is mounted inside the device housing. The pump has a pump actuator, a fluid inlet extending through the housing wall and a fluid outlet extending through the housing wall.

An electric motor is mounted inside the housing and is operatively coupled to the pump actuator. Device control circuitry is also mounted inside the housing and includes motor drive circuitry electrically coupled to control operation of the electric motor and functional to control operation of the electric motor. A battery mounted inside the housing provides power to the electric motor and to the device control circuitry.

The device control circuitry can optionally include an intracranial pressure input functional to receive CSF space pressure signals from a CSF space pressure sensor, an outlet pressure sensor input functional to receive outflow pressure signals from a CSF outflow pressure sensor, and a CSF fluid flow input functional to receive CSF flow signals from a CSF flow rate sensor. The processor is responsive to the CSF space pressure signals, the outflow pressure signals, and the CSF flow rate signals to calculate CSF space pressures, CSF outflow pressures, and CSF removal volumes.

In another aspect, a memory unit is functionally coupled to the processor and contains pump control instructions to cause the processor to regulate removal of CSF fluid by controlling the electric motor through the motor drive circuitry. A telemetry unit may be provided, including a transmitter operative to wirelessly transmit outside the patient's body data corresponding to CSF space pressures, CSF outflow pressures, and CSF removal volumes calculated by the processor.

In accordance with another aspect, the present invention is a system for collecting cerebrospinal fluid (CSF) from a CSF space in a patient's body and draining the CSF into a subcutaneous CSF drain space in the patient's body comprising. The system may include a CSF fluid collection catheter positioned in the CSF space, a CSF pump unit implanted in the subcutaneous tissues which has a fluid inlet and a fluid outlet.

An inlet tube fluidly connects the fluid collection catheter to the pump fluid inlet, the inlet tube being positioned subcutaneously in the patient's body between the CSF space and the CSF pump unit. A drain tube provides a subcutaneous fluid connection between the fluid outlet and the CSF drain space.

The CSF pump unit can include a fluid pump coupled to the fluid inlet and the fluid outlet and an electric motor mechanically coupled to the pump. A control unit is electrically coupled to the electric motor and controls operation of the electric motor to regulate flow of CSF fluid. A battery provides power to the electric motor and to the control unit.

In one embodiment of the system, the CSF pump unit includes a telemetry transmitter to wirelessly transmit CSF data outside the patient's body. The CSF data may include CSF space pressures, CSF drain pressures, and CSF flow volumes.

The device and system may further include a port on the device housing casing which allows percutaneous aspiration of CSF from within a reservoir or antechamber for sampling and analysis.

Each cycle of the pump removes a small but precise volume of CSF from the CSF space. The electronic controls of the device and system allow regulation of the volume to be removed, the time frame of the fluid removal, and modulation of flow through continuous monitoring of the pressure within the CSF space.

The device allows for wireless telemetry to report actual performance as well as providing values of the CSF space pressures and out flow pressures into the peritoneum or other drain space.

The CSF is collected from the brain or spine by silastic or similar tubing which is surgically implanted using standard neurosurgical techniques. Similar drain tubing is then connected to the outlet. The surgeon may implant this drain tubing into a suitable anatomic space that allows for the re-absorption of CSF, typified by the peritoneal cavity.

Preferably, the rechargeable battery is designed to allow for steady, continuous operation and is re-charged by application of a recharging coil brought into proximity of the device, outside the skin.

The pump may contain an audible alarm to warn of a low battery or malfunctioning status. The wireless telemetry may communicate the functional status of the pump, as well as allowing for diagnostic examination of its performance.

Through the wireless telemetry capabilities, the treating physician is able to adjust the volume of CSF to be removed to optimize treatment of the patient's condition.

A solid state memory unit is contained within the device housing to store data for download and analysis. Failsafe controls shut down the device if safe CSF volumes or flow rates are exceeded.

DETAILED DESCRIPTION OF THE INVENTION

Figure 1:
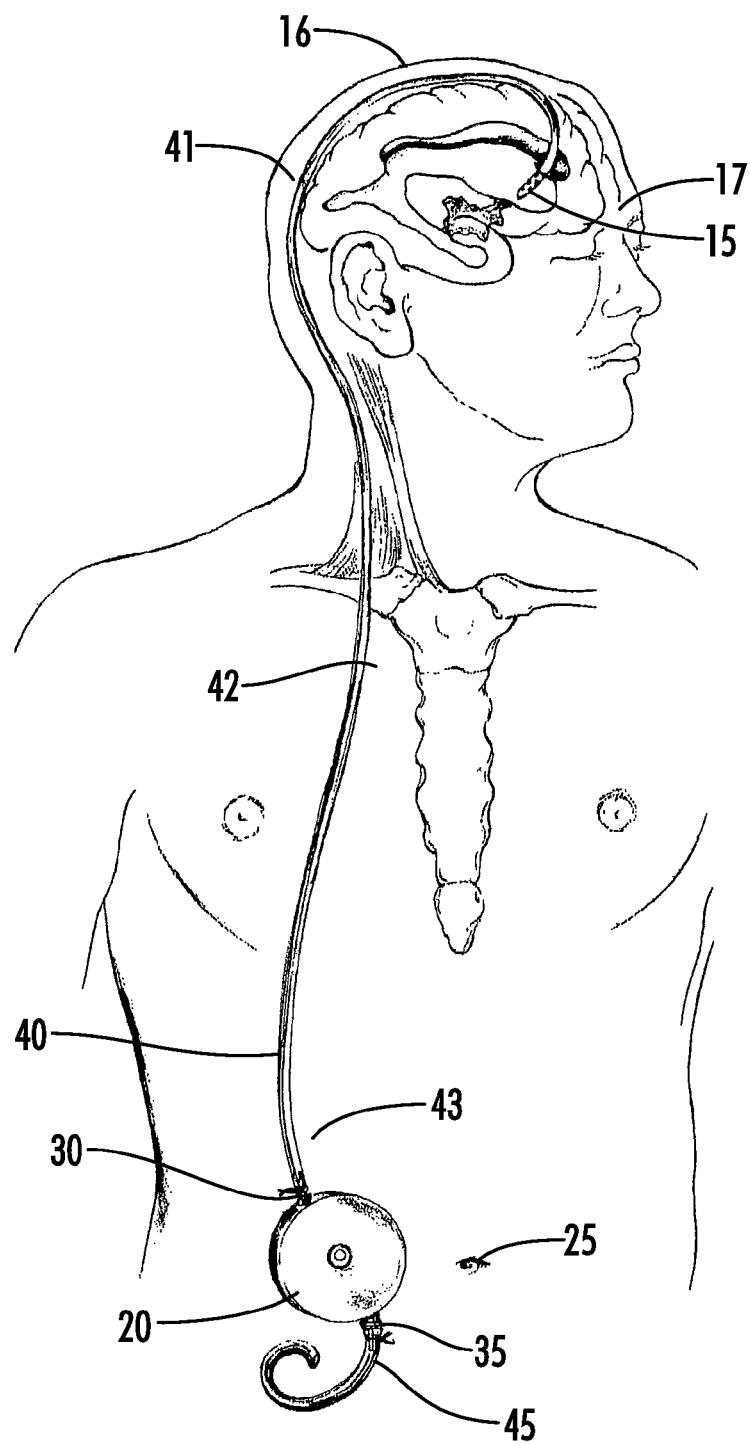
FIG. 1 is a phantom view of a patient in which one embodiment of the system of the present invention has been implanted for collecting CSF from the right lateral ventricle and draining it into the peritoneum.

One embodiment of CSF removal system of the present invention is shown in FIG. 1. Using a burr hole 16 positioned 2.5 cm from midline and 10-12 cm from the patient's nasion 17, a CSF collection catheter tip 15 is positioned in a patient's CSF space, in this case the anterior horn of the right lateral ventricle. A CSF pump unit 20 is implanted subcutaneously in fat near the patient's umbilicus 25. The pump unit 20 has a fluid inlet 30 and a fluid outlet 35.

An inlet tube 40 fluidly connects the catheter tip 15 (and CSF space) to the pump fluid inlet 30. In this embodiment, the distal section of tube 40 is positioned in the sublageal scalp 41 and brought through a subcutaneous tunnel 42 over the anterior chest and right side of the neck. The proximal section of inlet tube 40 is then anchored to the peritoneum 43 before connecting to pump inlet 30.

The pumping action of the pump unit 20 extracts CSF fluid from the CSF space through inlet tube 30. The proximal end of a subcutaneous outlet tube 45 is connected to pump outlet 35. The distal end of outlet tube 45 is positioned so as to drain the collected CSF fluid into a CSF drain space to be absorbed. In this embodiment, the CSF drain space is the patient's peritoneum.

In some embodiments the inlet and outlet tubes are made of conventional silastic tubing.

Figure 2:
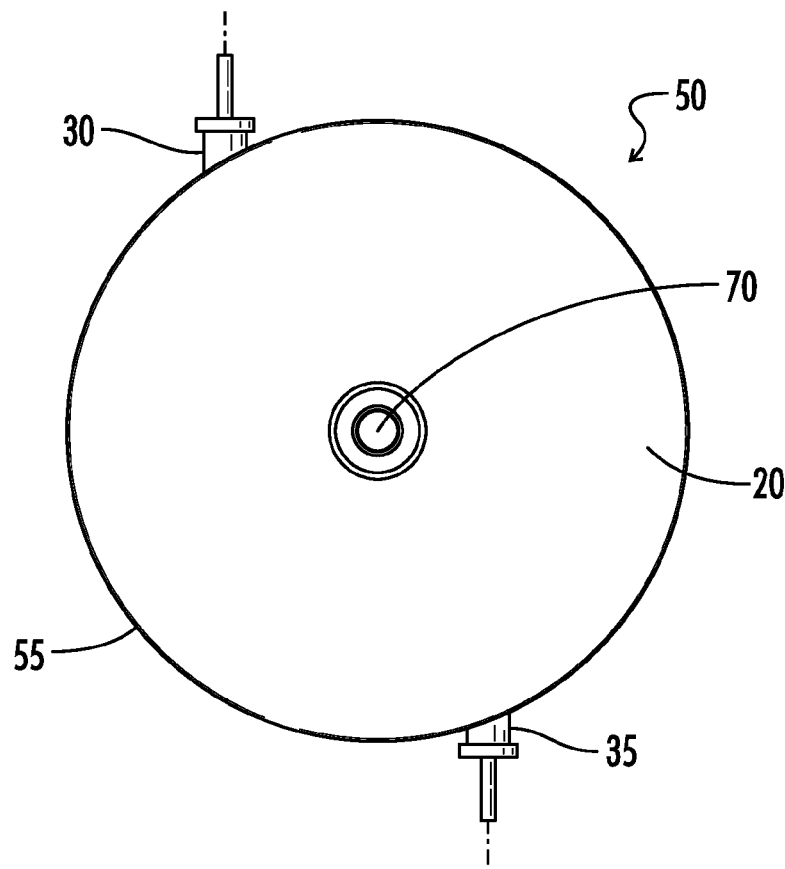
FIG. 2 is a top view of one embodiment of a CSF pump in accordance with the present invention.
Figure 3:
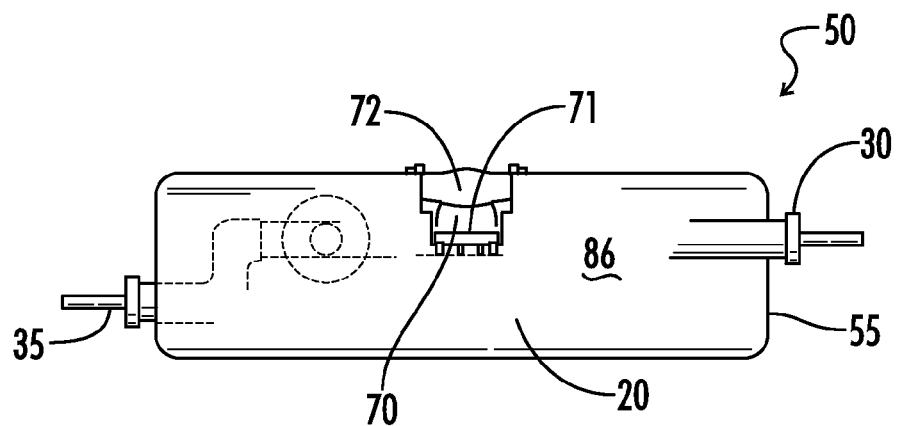
FIG. 3 is a partial cutaway side view of the CSF pump of FIG. 2.
Figure 4:
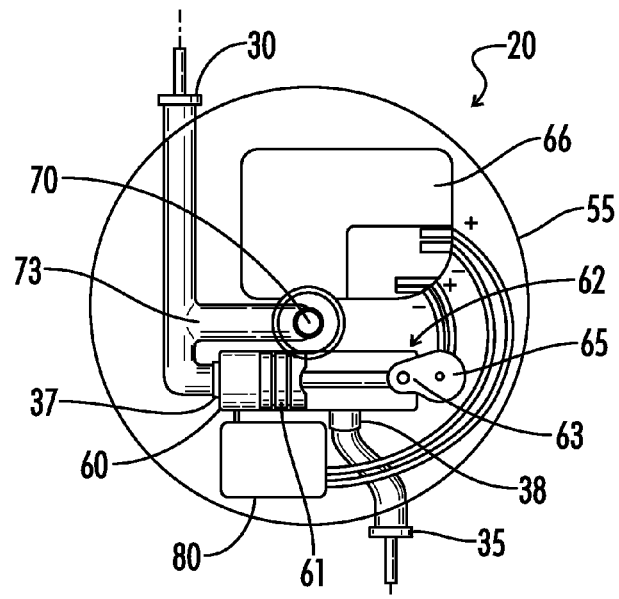
FIG. 4 is a plan view of the CSF pump of FIGS. 2 and 3, with the top surface of the pump housing removed to expose the interior components.

Referring now to FIGS. 2, 3, and 4, one embodiment of the pump unit 20 of the present invention is shown. The pump components are mounted inside a housing 50. The housing 50 preferably has an exterior housing wall 55 made of a material and having a shape adapted so that the pump 20 can be implanted subcutaneously in a patient. The pump inlet 30 and outlet 35 pass through the housing wall 55.

Inside the pump unit 20 is a fluid pump 60 fluidly coupled to the pump inlet 30 and outlet 35. In one embodiment, the pump 60 is a piston pump with a reciprocating piston 61 inside a pump cylinder 62. The piston 61 is driven by an actuator which in this embodiment is a cam 63. The cam 63 is mechanically coupled to an electric motor 65. Rotation of the electric motor shaft (not shown) causes the cam 63 to rotate, with a lobe on the cam causing the piston 62 to move in a reciprocating fashion linearly inside the cylinder 61. Thus, it can be seen that the rotational speed of the electric motor 65 will generally determine the rate at which CSF fluid is removed from the CSF space and drained into the CSF drain space.

Preferably, the pump inlet 30 and outlet 35 incorporate one-way valves 37 and 38 so that CSF can flow into and out of the pump 20 only in the intended directions.

The motor 65 is powered by a rechargeable battery 66. Preferably, the battery 66 can be charged using an external charger inductively coupled to a charging coil (not shown).

Figure 5:
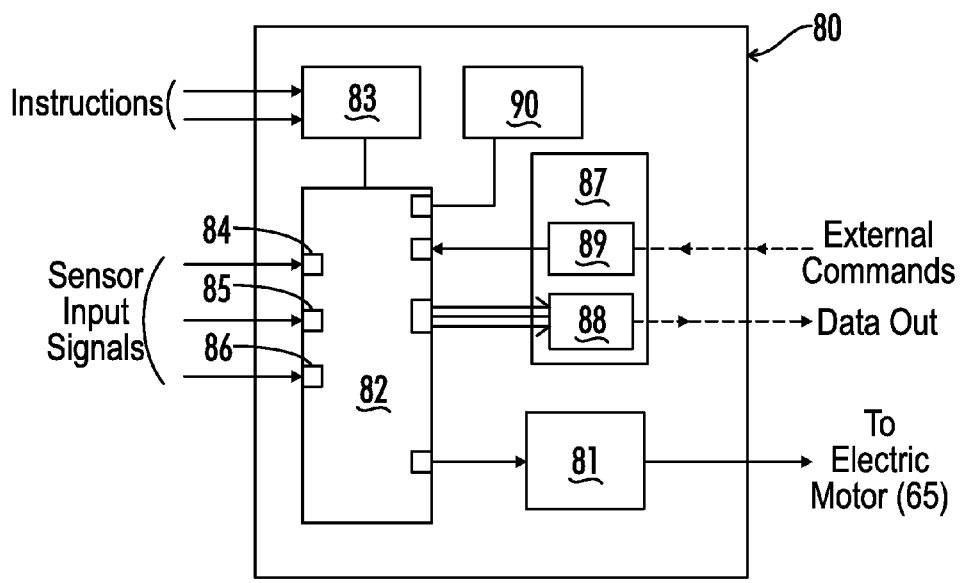
FIG. 5 is a block diagram of one embodiment of the control circuitry used in the present invention.

Referring also to FIG. 5, an electronic control unit or control circuitry 80 is mounted inside the housing 50 and is electrically connected to the electric motor 65 and to the battery 66. The control unit 80 includes motor drive circuitry 81 that powers and regulates the speed of the motor 65 using conventional analog or digital motor control logic well-known to persons of skill in the art.

The control unit 80 can further include a processor 82 and a memory unit 83. The processor 82 and memory unit 83 cooperate together and contain control logic and/or pump control instructions that cause the processor 82 (acting through the motor drive circuitry 81) to regulate the flow of CSF fluid in a manner programmed or commanded by the treating physician.

In one embodiment, the control unit 80 also has an intracranial pressure input 84 that receive CSF space pressure signals from a sensor (not shown) that senses and reports CSF pressure from within the CSF space. The control unit 80 can also include an outlet pressure sensor input 85 that receives outflow pressure signals from a CSF outflow pressure sensor (not shown) that monitors and reports CSF outlet pressure. Further, a CSF fluid flow input 86 can be incorporated in the control unit 80 to receive CSF flow rate signals from a CSF flow rate sensor (not shown) that measures the flow rate of CSF through the inlet tube 40. The flow rate data can then be used by the processor 80 to calculate the volume of CSF that has been removed from the CSF space during a period of time deemed relevant by the treating physician.

In a preferred embodiment, the control unit 80 also includes an internal telemetry unit 87. The internal telemetry unit 87 has a telemetry transmitter 88 that wirelessly transmits data outside the patient's body to an external telemetry unit (not shown). The data transmitted can include CSF space pressures, CSF outflow pressures, and CSF removal volumes calculated by the processor.

The internal telemetry unit 87 can also incorporate a telemetry receiver 89 that is coupled to the processor 82 and wirelessly receives commands transmitted from the external telemetry unit (not shown). These commands can cause the processor 82 to modify the pump control instructions that are stored in the memory unit 81. Accordingly, the treating physician can adjust the operation of the pump unit 20 to optimize removal of CSF from the patient's CSF space.

In one embodiment, the pump unit 20 further includes an antechamber 70 that is coupled to the pump inlet 30 through an auxiliary inlet tube 73. This allows the antechamber 70 to receive and store a small volume of CSF that is removed from the CSF space. The top of the antechamber 70 is sealed by a plenum 72 with a needle stop 71 positioned inside the antechamber 70. Referring to FIG. 3, the physician can pass an extraction needle (not shown) through the patient's skin and enter the antechamber 70 through the plenum 72. When the needle reaches the needle stop 71, a suitable amount of CSF can be removed from the patient for further examination.

In another embodiment, the control unit 80 can also include an alarm unit 90. In this embodiment, the processor 82 and memory unit 83 further include monitoring instructions that will activate the alarm unit 80 if there is a low battery condition and/or a pump malfunction is detected in the device. The alarm unit 90 can further respond to monitoring instructions and monitored flow rate and volume data to cause processor 82 to disable the pump 60 if predetermined CSF flow rate or volume limits are exceeded.

Thus, although there have been described particular embodiments of the present invention of a new and useful Implantable Pump for Removal of Cerebral Spinal Fluid it is not intended that such references be construed as limitations upon the scope of this invention except as set forth in the following claims.

What is claimed is:

1. A device for removing cerebrospinal fluid (CSF) from a CSF space within a patient's body by monitoring signals from a CSF space pressure sensor, an outlet pressure sensor and a CSF fluid flow rate sensor, the device comprising:
   a pump having a pump inlet and a pump outlet;
   an inlet tube having a first end coupled to the pump inlet and a second end in fluid communication with the CSF space within the patient's body;
   an antechamber defined on the pump, the antechamber being in fluid communication with the pump inlet, the antechamber positioned to collect a sample of CSF fluid traveling into the pump from the tube;
   a needle stop disposed in the antechamber;
   device control circuitry disposed on the pump;
   a CSF space pressure input disposed on the device control circuitry configured to acquire a CSF space pressure input signal from the CSF space pressure sensor, wherein the CSF space pressure input signal is representative of pressure in the CSF space;
   an outlet pressure sensor input disposed on the device control circuitry operable to acquire an outlet pressure input signal from the outlet pressure sensor;
   a CSF fluid flow rate input disposed on the device control circuitry operable to acquire a CSF fluid flow rate input signal from the CSF fluid flow rate sensor; and
   a processor disposed on the device control circuitry configured to receive and process the CSF space pressure input signal, the outlet pressure signal, and the CSF fluid flow rate signal;
   wherein the device control circuitry is selectively programmable in a first mode to instruct the pump to extract CSF fluid from the CSF space in response to detecting a predetermined level of the CSF space pressure input signal;
   wherein the device control circuitry is selectively programmable in a second mode to instruct the pump to extract CSF fluid from the CSF space in response to detecting a predetermined level of the outlet pressure signal; and
   wherein the device control circuitry is selectively programmable in a third mode to instruct the pump to extract CSF fluid from the CSF space in response to detecting a predetermined level of the CSF fluid flow rate signal.

2. The device of claim 1, further comprising:
   a catheter tip disposed on the distal end of the inlet tube, the catheter tip being open to the CSF space.

3. The device of claim 2, further comprising:
   a CSF space pressure sensor disposed in the CSF space,
   wherein the CSF space pressure sensor is operatively attached to the intracranial pressure sensor input on the device control circuitry.

4. The device of claim 3, wherein:
   the CSF space pressure sensor is an intracranial pressure sensor.

5. The device of claim 3, wherein:
   the processor is configured to calculate CSF space pressure, CSF outflow pressure, and CSF removal volume.

6. The device of claim 3, further comprising:
   a wireless telemetry transmitter disposed on the pump, the transmitter being configured to wirelessly transmit a data signal representative of the CSF space pressure, the CSF outflow pressure, and the CSF removal volume.

7. The device of claim 1, further comprising:
   a motor control circuit disposed on the device control circuitry;
   wherein the processor is operatively connected to the motor control circuit; and
   wherein the motor control circuit is configured to control the pump based on the CSF space pressure input signal, the outlet pressure signal, and the CSF fluid flow rate signal.

8. A device for removing cerebrospinal fluid (CSF) from a CSF space within a patient's body by monitoring a CSF space pressure sensor signal and a CSF fluid flow rate sensor signal, the device comprising: an implantable pump having a pump inlet and a pump outlet; an inlet tube having a first tube end in fluid communication with the pump inlet and a second tube end; a tube inlet port positioned at the second tube end, the tube inlet port configured to be positioned in fluid communication with the CSF space; an antechamber defined on the pump, the antechamber being in fluid communication with the pump inlet, the antechamber positioned to collect a sample of CSF fluid traveling into the pump from the inlet tube; and device control circuitry disposed on the implantable pump; wherein the device control circuitry is selectively programmable to instruct the pump to extract CSF fluid from the CSF space in response to detecting a predetermined level of the CSF space pressure sensor signal or a predetermined level of the CSF fluid flow rate sensor signal.

9. The device of claim 8, further comprising:
   a catheter tip disposed on the tube inlet port.

10. The device of claim 8, further comprising:
    a check valve disposed on the inlet tube between the tube inlet port and the pump.

11. The device of claim 8, further comprising:
    an outlet tube coupled to the pump outlet.

12. The device of claim 11, further comprising:
    a check valve disposed between the pump and the outlet tube, the check valve configured to prevent fluids from travelling upstream from the outlet tube into the pump.

13. The device of claim 12, further comprising:
    a wireless telemetry transmitter disposed on the pump, the transmitter being configured to wirelessly transmit a data signal representative of CSF space pressure, CSF outflow pressure, and CSF removal volume.

14. The apparatus of claim 8, further comprising intracranial CSF space pressure sensor input located on the device control circuitry; and a CSF space pressure sensor disposed in the CSF space, wherein the CSF space pressure sensor is operatively attached to the CSF space pressure sensor input on the device control circuitry.

* * * * *